(12) United States Patent
Natarajan et al.

(10) Patent No.: US 8,714,430 B2
(45) Date of Patent: May 6, 2014

(54) INDICATOR FOR SURGICAL STAPLER

(75) Inventors: Anandram Natarajan, Chennai-Tamil Nadu (IN); Srinivasan Selvaraj, Chennai-Tamil Nadu (IN)

(73) Assignee: Covidien LP, Mansfield, MA (US)

( * ) Notice: Subject to any disclaimer, the term of this patent is extended or adjusted under 35 U.S.C. 154(b) by 532 days.

(21) Appl. No.: 12/953,603

(22) Filed: Nov. 24, 2010

(65) Prior Publication Data

US 2011/0155782 A1    Jun. 30, 2011

Related U.S. Application Data (60) Provisional application No. 61/291,453, filed on Dec. 31, 2009.

(51) Int. Cl.
    *A61B 17/068*    (2006.01)
(52) U.S. Cl.
    USPC ............... 227/176.1; 227/175.1; 227/120; 227/19; 606/219
(58) Field of Classification Search
    CPC ............ A61B 17/068; A61B 17/07207
    USPC .......... 227/176.1, 120, 19, 175.1; 606/219
    See application file for complete search history.

(56) References Cited

U.S. PATENT DOCUMENTS

| | | | |
|---|---|---|---|
| 4,379,457 A | 4/1983 | Gravener et al. | |
| 4,527,724 A | 7/1985 | Chow et al. | |
| 4,892,244 A | 1/1990 | Fox et al. | |
| 4,951,860 A * | 8/1990 | Peters et al. | 227/177.1 |
| 5,005,749 A | 4/1991 | Aranyi | |
| 5,071,052 A | 12/1991 | Rodak | |
| 5,271,544 A | 12/1993 | Fox et al. | |
| 5,275,322 A | 1/1994 | Brinkerhoff et al. | |
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,403,312 A | 4/1995 | Yates et al. | |
| 5,443,198 A | 8/1995 | Viola et al. | |
| 5,464,144 A | 11/1995 | Guy et al. | |
| 5,474,223 A | 12/1995 | Viola et al. | |

(Continued)

FOREIGN PATENT DOCUMENTS

| | | |
|---|---|---|
| EP | 0570915 A2 | 11/1993 |
| EP | 0639349 A2 | 2/1995 |

(Continued)

OTHER PUBLICATIONS

US 5,826,777, 10/1998, Green et al. (withdrawn).

*Primary Examiner* — Michelle Lopez (57) ABSTRACT

A surgical stapler for visually indicating to a user the stage of operation of the stapler. The surgical stapler includes a body, a stapling assembly positioned on a distal end of the body including a cartridge assembly and an anvil assembly, and a thrust bar slidably disposed within the body. The thrust bar is configured to advance distally from a retracted position to a first advanced position during approximation of the cartridge assembly towards the anvil assembly and advance further to a second advanced position to cause the release of staples from the cartridge assembly. An indicator member is connected to the thrust bar and configured to provide visual indication to a user upon complete approximation of the cartridge assembly and upon release of staples from the cartridge assembly.

19 Claims, 8 Drawing Sheets

(56) References Cited

U.S. PATENT DOCUMENTS

| | | | |
|---|---|---|---|
| 5,487,499 | A | 1/1996 | Sorrentino et al. |
| 5,503,320 | A | 4/1996 | Webster et al. |
| 5,529,235 | A | 6/1996 | Boiarski et al. |
| 5,533,661 | A | 7/1996 | Main et al. |
| 5,535,934 | A | 7/1996 | Boiarski et al. |
| 5,535,937 | A | 7/1996 | Boiarski et al. |
| 5,588,579 | A | 12/1996 | Schnut et al. |
| 5,607,436 | A | 3/1997 | Pratt et al. |
| 5,639,008 | A | 6/1997 | Gallagher et al. |
| 5,685,474 | A | 11/1997 | Seeber |
| 5,688,270 | A | 11/1997 | Yates et al. |
| 5,697,543 | A | 12/1997 | Burdorff |
| 5,709,680 | A | 1/1998 | Yates et al. |
| 5,758,814 | A | 6/1998 | Gallagher et al. |
| 5,762,255 | A | 6/1998 | Chrisman et al. |
| 5,797,537 | A | 8/1998 | Oberlin et al. |
| 5,799,857 | A | 9/1998 | Robertson et al. |
| 5,807,393 | A | 9/1998 | Williamson, IV et al. |
| 5,810,811 | A | 9/1998 | Yates et al. |
| 5,820,009 | A | 10/1998 | Melling et al. |
| 5,833,690 | A | 11/1998 | Yates et al. |
| 5,882,340 | A | 3/1999 | Yoon |
| 5,915,616 | A | 6/1999 | Viola et al. |
| 6,010,054 | A | 1/2000 | Johnson et al. |
| 6,024,741 | A | 2/2000 | Williamson, IV et al. |
| 6,050,472 | A | 4/2000 | Shibata |
| 6,053,390 | A | 4/2000 | Green et al. |
| 6,066,145 | A | 5/2000 | Wurster |
| H1904 | H | 10/2000 | Yates et al. |
| 6,269,997 | B1 | 8/2001 | Balazs et al. |
| 6,601,748 | B1 | 8/2003 | Fung et al. |
| 6,769,594 | B2 | 8/2004 | Orban, III |
| 6,945,444 | B2 | 9/2005 | Gresham et al. |
| 6,957,758 | B2 | 10/2005 | Aranyi |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,159,750 | B2 | 1/2007 | Racenet et al. |
| 7,168,604 | B2 | 1/2007 | Milliman et al. |
| 7,179,267 | B2 | 2/2007 | Nolan et al. |
| 7,234,624 | B2 | 6/2007 | Gresham et al. |
| 7,237,708 | B1 | 7/2007 | Guy et al. |
| 7,303,106 | B2 | 12/2007 | Milliman et al. |
| 7,325,713 | B2 | 2/2008 | Aranyi |
| 7,364,060 | B2 | 4/2008 | Milliman |
| 7,364,061 | B2 | 4/2008 | Swayze et al. |
| 7,431,191 | B2 | 10/2008 | Milliman |
| 7,464,847 | B2 | 12/2008 | Viola et al. |
| 7,516,877 | B2 | 4/2009 | Aranyi |
| 7,546,940 | B2 | 6/2009 | Milliman et al. |
| 7,556,186 | B2 | 7/2009 | Milliman |
| 7,766,210 | B2 | 8/2010 | Shelton, IV et al. |
| 7,770,775 | B2 | 8/2010 | Shelton, IV et al. |
| 7,802,712 | B2 | 9/2010 | Milliman et al. |
| 7,810,692 | B2 | 10/2010 | Hall et al. |
| 7,845,534 | B2 | 12/2010 | Viola et al. |
| 7,845,537 | B2 | 12/2010 | Shelton, IV et al. |
| 7,857,187 | B2 | 12/2010 | Milliman |
| 7,870,989 | B2 | 1/2011 | Viola et al. |
| 8,056,787 | B2 * | 11/2011 | Boudreaux et al. ........ 227/176.1 |
| 2004/0195289 | A1 | 10/2004 | Aranyi |
| 2005/0006432 | A1 | 1/2005 | Racenet et al. |
| 2005/0006433 | A1 | 1/2005 | Milliman et al. |
| 2005/0023325 | A1 | 2/2005 | Gresham et al. |
| 2005/0067457 | A1 | 3/2005 | Shelton, IV et al. |
| 2005/0067458 | A1 | 3/2005 | Swayze et al. |
| 2005/0103819 | A1 | 5/2005 | Racenet et al. |
| 2005/0116009 | A1 | 6/2005 | Milliman |
| 2005/0205639 | A1 | 9/2005 | Milliman |
| 2005/0205640 | A1 | 9/2005 | Milliman |
| 2006/0025816 | A1 | 2/2006 | Shelton, IV |
| 2006/0097025 | A1 | 5/2006 | Milliman et al. |
| 2006/0175375 | A1 | 8/2006 | Shelton, IV et al. |
| 2006/0201992 | A1 | 9/2006 | Racenet |
| 2006/0212069 | A1 | 9/2006 | Shelton, IV |
| 2006/0219752 | A1 | 10/2006 | Arad et al. |
| 2006/0235437 | A1 | 10/2006 | Vitali et al. |
| 2006/0235438 | A1 | 10/2006 | Huitema et al. |
| 2006/0235439 | A1 | 10/2006 | Molitor et al. |
| 2006/0235440 | A1 | 10/2006 | Huitema et al. |
| 2006/0235441 | A1 | 10/2006 | Huitema et al. |
| 2006/0235442 | A1 | 10/2006 | Huitema |
| 2006/0235443 | A1 | 10/2006 | Huitema et al. |
| 2006/0235444 | A1 | 10/2006 | Huitema et al. |
| 2006/0273135 | A1 | 12/2006 | Beetel |
| 2006/0278680 | A1 | 12/2006 | Viola et al. |
| 2007/0034670 | A1 | 2/2007 | Racenet et al. |
| 2007/0060952 | A1 | 3/2007 | Roby et al. |
| 2007/0075117 | A1 | 4/2007 | Milliman et al. |
| 2007/0078486 | A1 | 4/2007 | Milliman et al. |
| 2007/0108252 | A1 | 5/2007 | Racenet et al. |
| 2007/0175964 | A1 | 8/2007 | Shelton, IV et al. |
| 2007/0272722 | A1 | 11/2007 | Aranyi |
| 2008/0135600 | A1 * | 6/2008 | Hiranuma et al. ........ 227/176.1 |
| 2008/0142566 | A1 | 6/2008 | Gresham et al. |
| 2008/0230581 | A1 | 9/2008 | Marczyk et al. |
| 2008/0237298 | A1 | 10/2008 | Schall |
| 2008/0312687 | A1 | 12/2008 | Blier |
| 2009/0179063 | A1 | 7/2009 | Milliman et al. |
| 2009/0250502 | A1 | 10/2009 | Milliman |
| 2010/0038401 | A1 | 2/2010 | Milliman et al. |
| 2010/0327041 | A1 | 12/2010 | Milliman et al. |

FOREIGN PATENT DOCUMENTS

| | | |
|---|---|---|
| EP | 1658813 A1 | 5/2006 |
| EP | 1857058 A1 | 11/2007 |
| EP | 1997438 | 12/2008 |
| EP | 2090255 | 8/2009 |

* cited by examiner

INDICATOR FOR SURGICAL STAPLER

This application claims priority from provisional application Ser. No. 61/291,453, filed Dec. 31, 2009, the entire contents of which are incorporated herein by reference.

BACKGROUND

1. Technical Field

The present disclosure relates generally to a surgical stapling apparatus and, more specifically, to a surgical stapling apparatus having a mechanism for indicating to a surgeon the condition of the stapler.

2. Background of Related Art

Surgical stapling instruments used for applying parallel rows of staples through compressed living tissue are well known in the art, and are commonly used, for example, for closure of tissue or organs prior to trans-section, prior to resection, or in anastomoses, and for occlusion of organs in thoracic and abdominal procedures.

Typically, such surgical stapling instruments include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. The approximation mechanism and the firing mechanism generally include distinct actuators for effecting approximation and firing of the staples.

A continuing need exists for a surgical stapling instrument which provides a clinician with visual indication of the stage of actuation of the surgical stapler.

SUMMARY

A surgical stapler configured for visually indicating to a user the stage of operation of the stapler is provided. In one aspect, the surgical stapler includes a body, a stapling assembly positioned on a distal portion of the body and including a cartridge assembly and an anvil assembly. A thrust bar is slidably disposed within the body and configured to advance distally from a retracted position to a first advanced position during approximation of the cartridge assembly towards the anvil assembly and advance further to a second advanced position to cause the release of staples from the cartridge assembly. An indicator member is connected to the thrust bar and configured to provide visual indication to a user upon complete approximation of the cartridge assembly and upon release of staples from the cartridge assembly.

In one embodiment, the distal end of the thrust bar may be configured for operable engagement with the stapling assembly to cause the ejection of staples from the cartridge assembly during the release of staples from the cartridge assembly. The body can include at least one window for viewing the indicator member. The indicator member may further be configured to indicate the stapler is ready to be approximated. In some embodiments, the indicator member is slidably mounted within the body. In other embodiments, the indicator member is rotatably mounted within the body. The indicator member may include a first symbol to indicate completion of the approximation stroke and a second symbol to indicate the release of staples from the cartridge assembly.

In one embodiment, the indicator member is rotatably mounted to the thrust bar. In some embodiments, the body may include a rack operably connected to the thrust bar. The rack may include a base, a pair of link members and a pair of toothed extensions operably engaged with the indicator members. Advancement of the thrust bar may cause rotation of the indicator member.

In one embodiment, an indicator member is slidable along with the thrust bar.

In another aspect, the present disclosure provides a surgical stapler comprising a body, a stapling assembly positioned on a distal portion of the body and including a cartridge assembly and an anvil assembly. A thrust bar is slidably disposed within the body and configured to advance distally from a retracted position to a first advanced position. An indicator member is configured to provide visual indication to a user upon at least one of complete approximation of the cartridge assembly and release of staples from the cartridge assembly. A rack is operably connected to the thrust bar and has a pair of toothed extensions, the toothed extensions being operably engaged with the indicator member and advancement of the thrust bar causes rotation of the indicator member.

In some embodiments, the indicator member is rotatable about an axis perpendicular to the longitudinal axis of the thrust bar. In some embodiments, the indicator member includes a first symbol to indicate complete approximation of the cartridge assembly and a second symbol to indicate release of staples from the cartridge assembly.

BRIEF DESCRIPTION OF THE DRAWINGS

Embodiments of the presently disclosed surgical stapling apparatus are described herein with reference to the drawings, wherein.

DETAILED DESCRIPTION

Embodiments of the presently disclosed surgical stapler will now be described in detail with reference to the drawings, wherein like reference numerals designate corresponding elements in each of the several views. Throughout this description, the term "proximal" will refer to the portion of the instrument closer to the operator and the term "distal" will refer to the portion of the instrument further from the operator.

Figure 1:
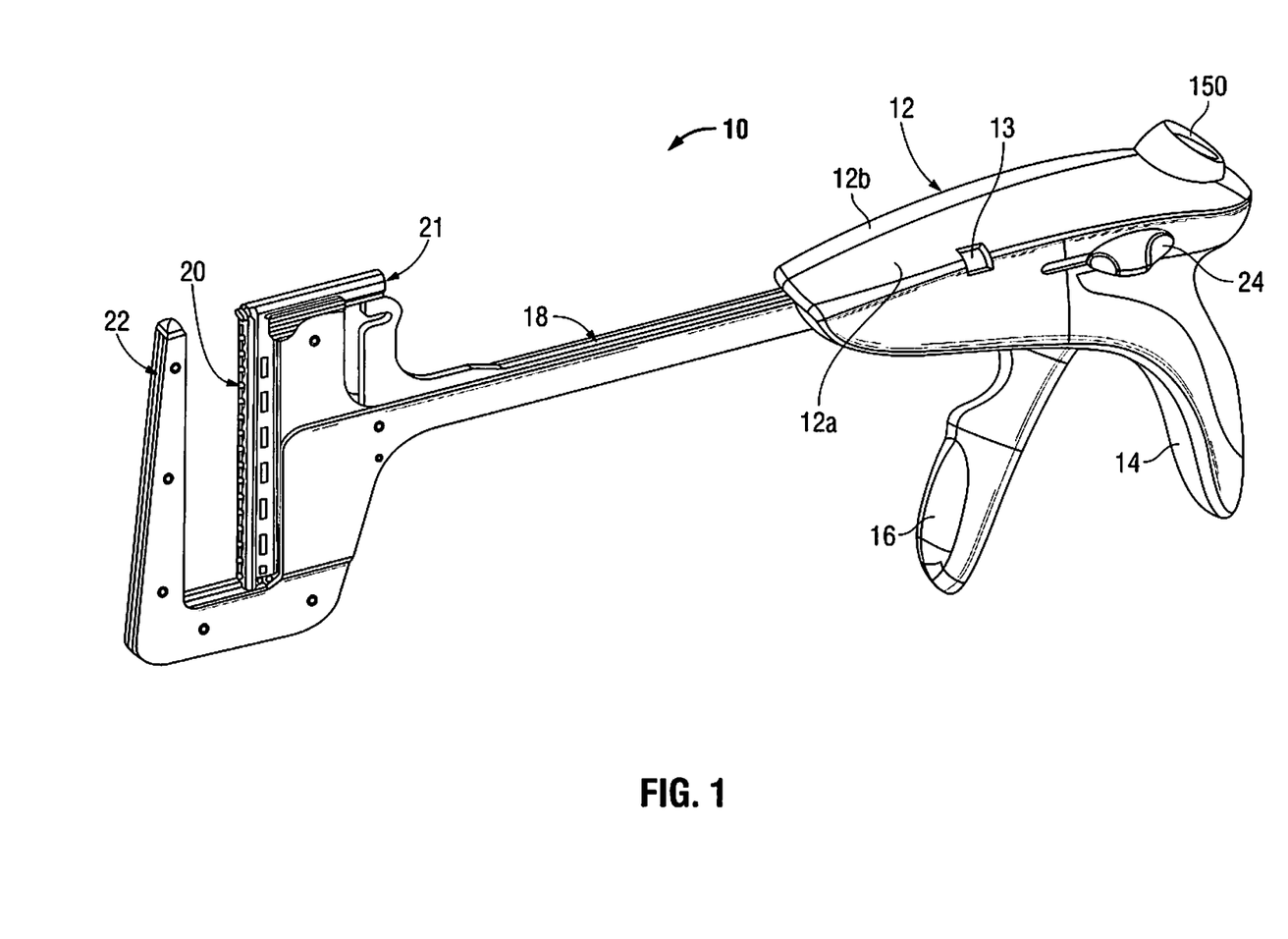
FIG. 1 is a perspective view of an embodiment of a surgical stapler in accordance with the present disclosure.

With reference to FIG. 1, a surgical stapling device according to an embodiment of the present disclosure is shown generally as surgical stapler 10. Surgical stapler 10 includes a body 12 defining a stationary handle 14, a pivotable trigger 16, an elongated central body portion 18, a cartridge assembly 20 and an anvil assembly 22. A thumb button 24 is slidably positioned on each side of body 12. Thumb buttons 24 are movable distally to manually advance an alignment pin 38 (FIG. 4) from alignment pin assembly 21 into engagement with anvil assembly 22 to capture tissue between anvil assembly 22 and cartridge assembly 20. A release button 150 of a release mechanism (not shown) is positioned on the proximal end of body 12 and is depressible to allow cartridge assembly 20 to return from an approximated position disposed adjacent to anvil assembly 22 to an unapproximated position spaced from anvil assembly 22 (as shown).

With continued reference to FIG. 1, body 12 is formed from a pair of molded half-sections 12a, 12b. In one embodiment, half-sections 12a, 12b are formed of plastic, although half-sections 12a, 12b may be formed of other materials, including metal. A cutout or window 13 is formed in each of half-sections 12a, 12b. Windows 13 may include a clear cover (not shown) to prevent debris from entering body 12. As will be discussed in further detail below, windows 13 are configured to align with an operably positioned indicator member mounted within body 12.

The internal structure and function of surgical stapler 10 will now be described to the extent necessary to fully disclose the aspects of the present disclosure. A more detailed discussion of the internal structure and function of the surgical stapler is disclosed U.S. Pat. No. 6,817,508 (the '508 patent), the entire contents of which are incorporated by reference herein. Although described with reference to surgical stapler 10, the aspects of present disclosure may be modified for use with any device having a multi-stage firing sequence. Also, the term surgical stapling as used herein includes application of two part fasteners.

Figure 2:
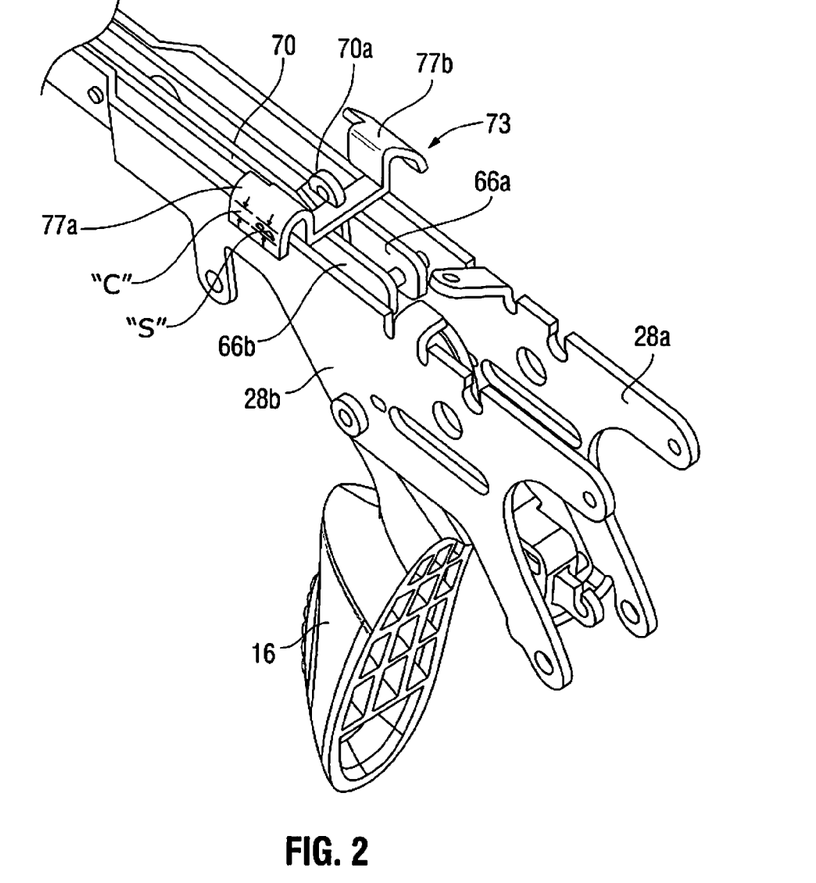
FIG. 2 is a perspective view of a portion of the surgical stapler of FIG. 1 showing the indicator mounted within the surgical stapler.

Referring now to FIG. 2, surgical stapler 10 includes a pair of clamp slide members 66a, 66b and a thrust bar 70. Clamp slide members 66a, 66b and thrust bar 70 are slidably supported between frame members 28a, 28b of surgical stapler 10 for movement between retracted and advanced positions in response to movement of trigger 16 through an approximation stroke and a stapling (staple firing) stroke. As will be discussed in further detail below, thrust bar 70 advances distally during the approximation stroke and advances further distally during the stapling (staple firing) stroke. Cartridge assembly 20 is operably supported at a distal end (not shown) of clamp slide members 66a, 66b such that advancement of clamp slide members 66a, 66b effects advancement of cartridge assembly 20. Cartridge assembly 20 is operably connected at a distal end (not shown) of thrust bar 70 such that advancement during the stapling stroke effects ejection of staples from cartridge assembly 20 into contact with anvil pockets on anvil assembly 20. Thrust bar 70 includes a flange 70a formed in a proximal end thereof. Flange 70a is configured to be operably engaged by indicator member 73.

Figure 3:
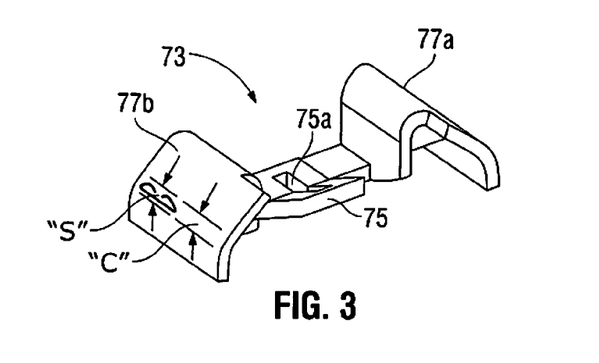
FIG. 3 is a perspective view of the indicator of FIG. 2.

Turning now to FIG. 3, indicator member 73 includes a base 75 and a pair of extensions or wings 77a, 77b. Base 75 is configured for operable engagement with flange 70a of thrust bar 70. In one embodiment, and as shown, base 75 includes an opening or slot 75a configured to be received about flange 70a. Indicator member 73 may, however, be operably engaged with thrust bar 70 in other suitable manners, including using adhesives and/or mechanical fasteners. In another embodiment, indicator member 73 is integrally formed with thrust bar 70. Extensions 77a, 77b extend radially outwardly from base 75 and are configured to slide along respective frame members 28a, 28b during advancement of thrust bar 70. Extensions 77a, 77b are mirror images of one another with each including a clamp symbol "C" and a staple symbol on their outer arcuate surfaces. Symbols "C", "S" may be pictures or icons, as shown, or may include one or more numbers, one or more letters, one or more colors, or any combination thereof or other indicia. Symbols "C", "S" are horizontally aligned on each of extensions 77a, 77b, and as will be discussed below, are located to be viewed through window 13 formed in each of half sections 12a, 12b. Although shown including only two symbols, extensions 77a, 77b may be modified, i.e., lengthened, to include a third, pre-clamped symbol (not shown).

Figures 4, 5:
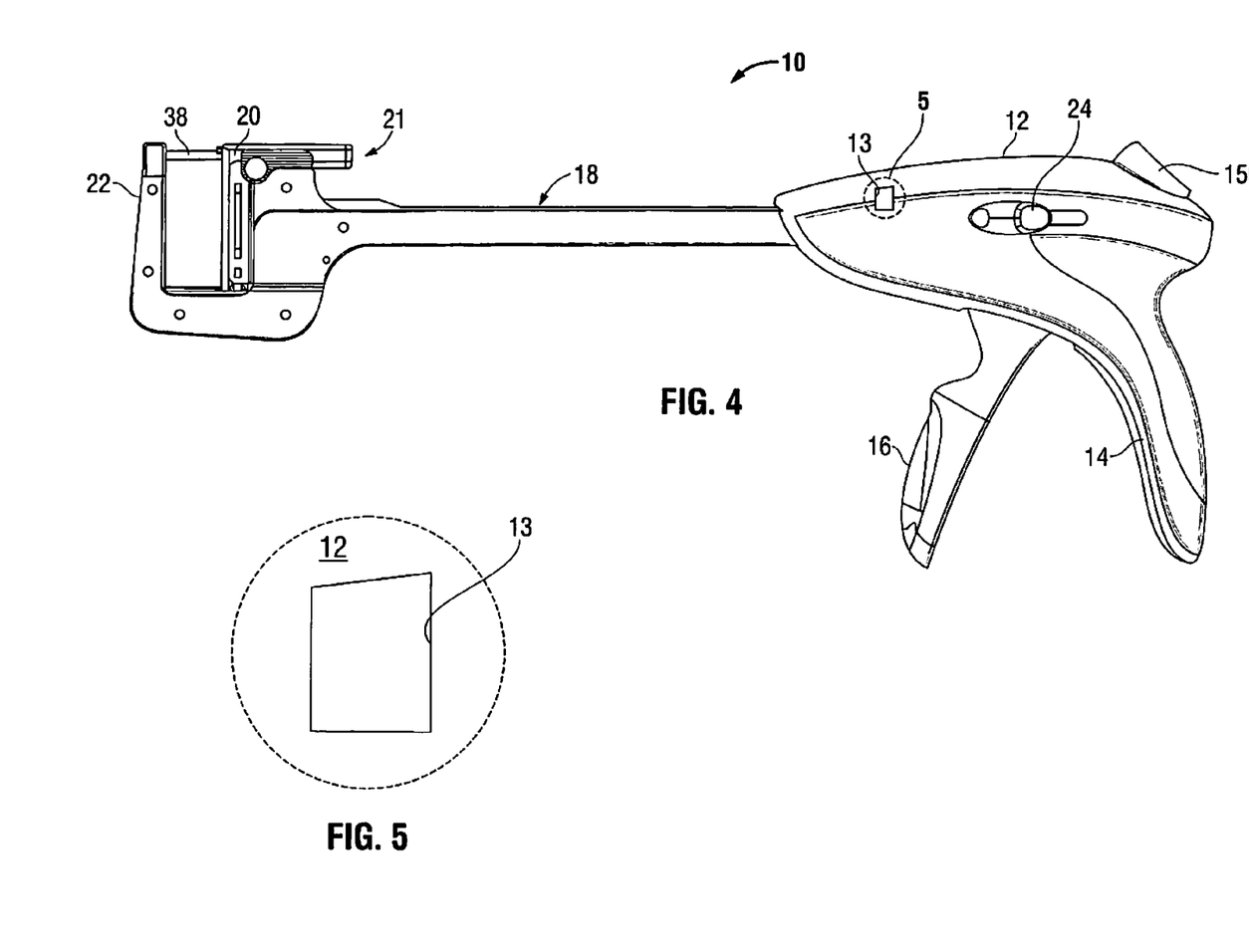
FIG. 4 is a side view of the surgical stapler of FIG. 1 in a pre-clamped (unapproximated) condition and with an alignment pin having been manually advanced.
FIG. 5 is an enlarged view of the indicated area of detail of FIG. 4, showing no symbol in the window.

The operation of surgical stapler 10 and indicator member 73 will now be described with reference to FIGS. 4-9. Referring initially to FIGS. 4 and 5, surgical stapler 10 is shown in a first or pre-clamped (unapproximated) condition. As shown, an alignment pin 38 has been manually advanced using thumb buttons 24; however, alignment pin 38 may instead be automatically advanced during the approximation stroke of trigger 16. In the first or pre-clamped condition, neither indicator member 73 nor either of symbols "C", "S" formed thereon are visible through window 13 of half sections 12a, 12b. As discussed above, in an alternative embodiment, extensions 77a, 77b are lengthened and include a third, pre-clamped symbol which is horizontally aligned with symbols "C", "S" and would be visible through window 13 when surgical stapler 10 is in a pre-clamped condition. In another embodiment, symbols "C", "S" are formed on half-sections 12a, 12b and extensions 77a, 77b include an arrow (not shown). In this manner, advancement of indicator member 73 causes sequential alignment of the arrow with a respective symbol "C", "S" during the clamping and stapling operations of surgical stapler 10.

Figures 6, 7:
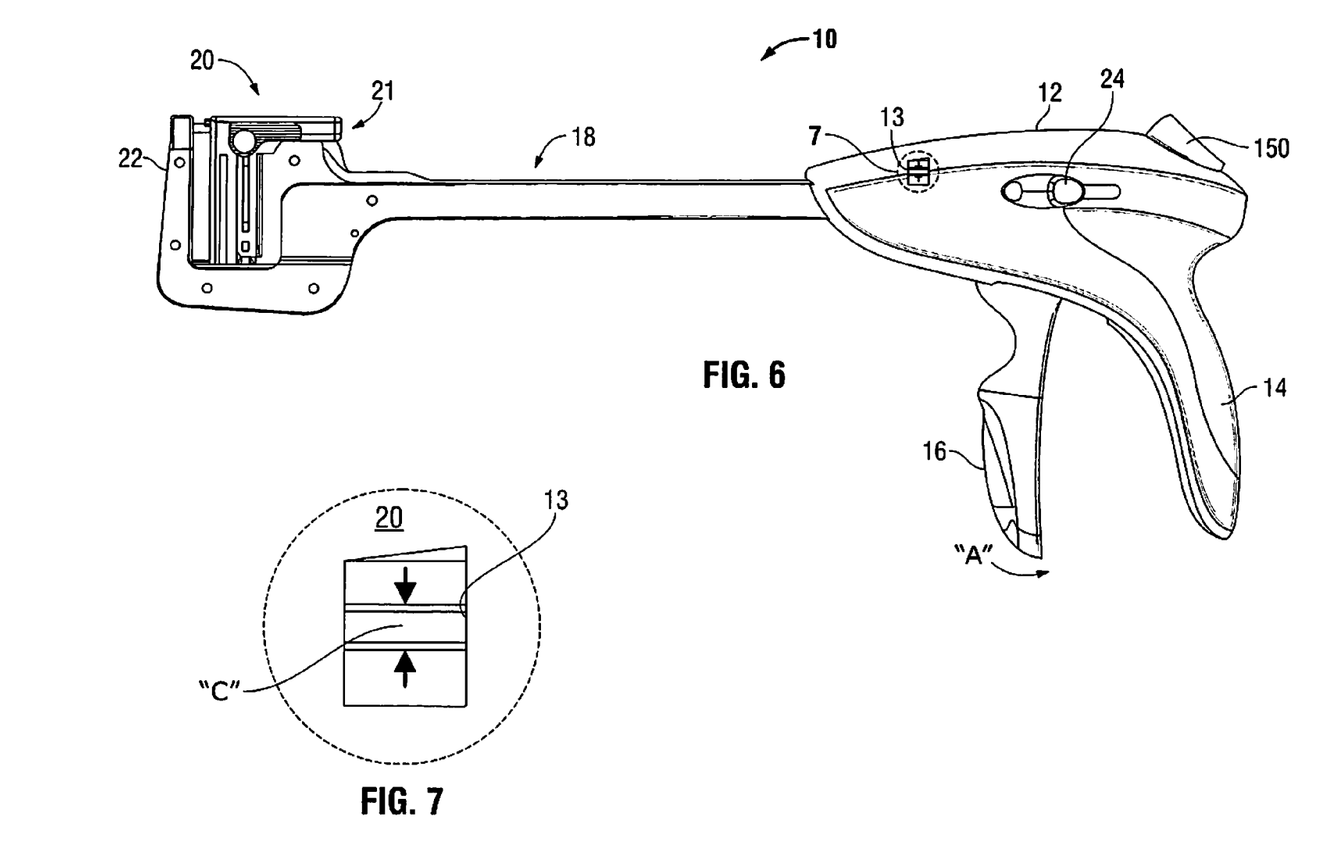
FIG. 6 is a side view of the surgical stapler of FIG. 1 in a clamped (approximated) condition.
FIG. 7 is an enlarged view of the indicated area of detail of FIG. 6 showing a clamp symbol.

FIGS. 6 and 7 illustrate surgical stapling device 10 during the approximation stroke of trigger 16. As illustrated, trigger 16 is moved towards stationary handle 14, in the direction indicated by arrow "A", to advance clamp slides 66a, 66b (FIG. 2) from a retracted position towards the advanced or approximated position, as described in detail in the '508 patent. As clamp slides 66a, 66b are advanced, thrust bar 70 (FIG. 2) is simultaneously advanced. As discussed above, advancement of thrust bar 70 causes advancement of indicator member 73. Indicator member 73 and window 13 formed in each of half sections 12a, 12b are arranged such that upon completion of the approximation stroke, clamp symbol "C" is completely visible through window 13. In this manner, a clinician receives visual indication that the clamping stage is complete and that surgical stapler 10 is in a clamped condition. If, during the approximation stroke, the surgical stapler 10 is not fully approximated, clamp symbol "C" would not be visible or would only be partially visible through windows 13. Anything less than a completely visible clamp symbol "C" would visually indicate to the clinician that surgical stapler 10 is not properly approximated.

As described in detail in the '508 patent, after the approximation stroke of trigger 16 is completed, trigger 16 returns to a non-compressed position upon its release to ready surgical stapler 10 for the stapling stroke. Prior to the stapling stroke, tissue (not shown) is captured between cartridge assembly 20 and anvil assembly 22. Alignment pin 38 (FIG. 4) maintains or captures the tissue between cartridge assembly 20 and anvil assembly 22.

Figures 8, 9:
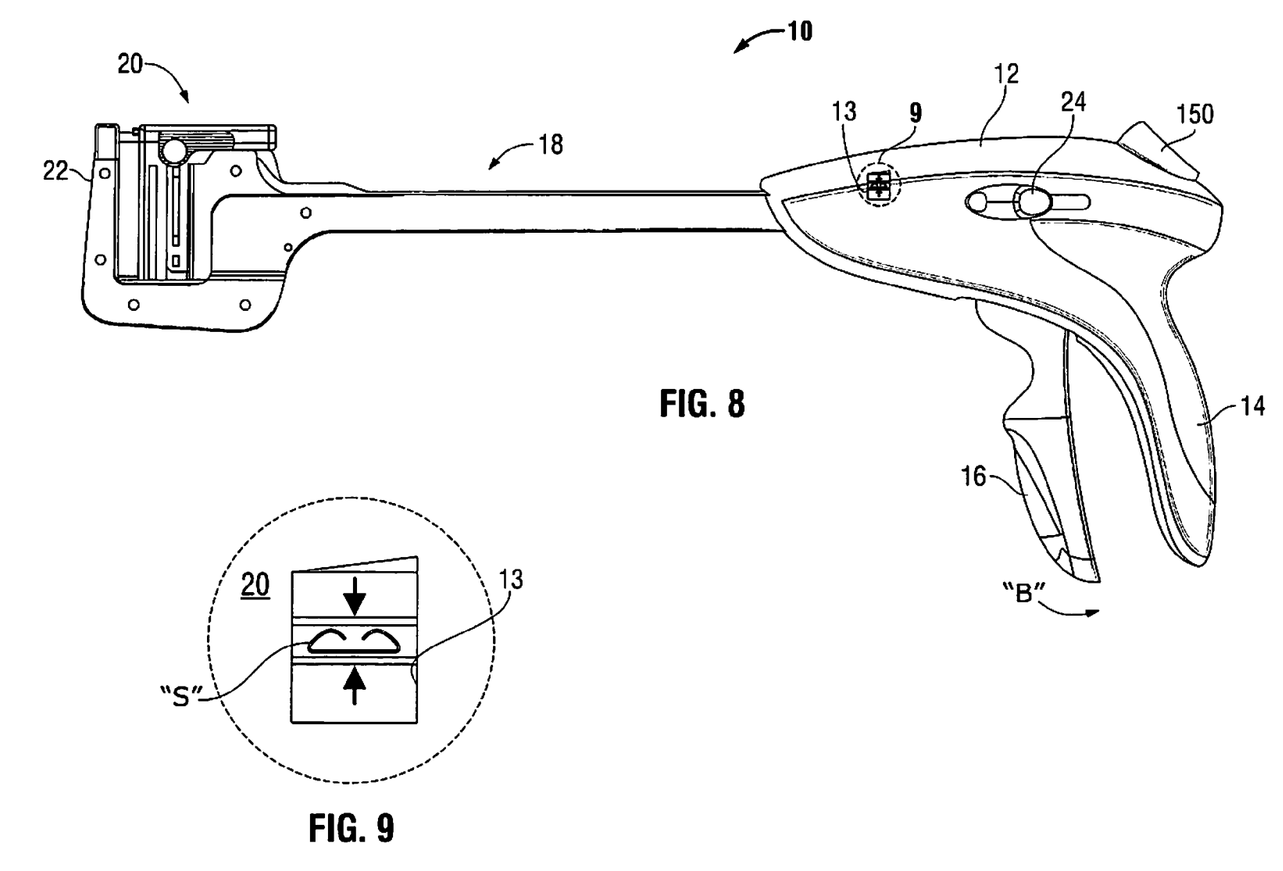
FIG. 8 is a side view of the surgical stapler of FIG. 1 in a fired condition.
FIG. 9 is an enlarged view of the indicated area of detail of FIG. 8 showing a stapled (fired) symbol.

FIGS. 8 and 9 illustrate surgical stapler 10 after trigger 16 has been moved through the stapling stroke, as indicated by arrow "B". During the stapling stroke, thrust bar 70 (FIG. 2) continues to distally advance within body 12. As noted above, advancement of thrust bar 70 causes advancement of indicator member 73. Upon completion of the stapling stroke, indicator member 73 has advanced to a position which staple symbol "S" is completely visible through window 13 of half-sections 12a, 12b. As discussed above with regard to the approximation stroke, if following the stapling stroke, staple symbols "S" are not completely visible through windows 13, the clinician is provided with visual indication that the staples of surgical stapler 10 have not been properly fired.

With continued reference to FIG. 8, upon completion of the stapling stroke, release button 150 is depressed and a spring (not shown) returns thrust bar 70 (FIG. 2) and clamp slide members 66a, 66b (FIG. 2) proximally to the initial or pre-clamped position. In one embodiment, and as shown, in the pre-clamped position, indicator member 73 is not visible through windows 13. In another embodiment, in the pre-clamped position, a pre-clamped symbol (not shown) is visible. In either instance, surgical stapler 10 is ready for reloading and use.

Figure 10:
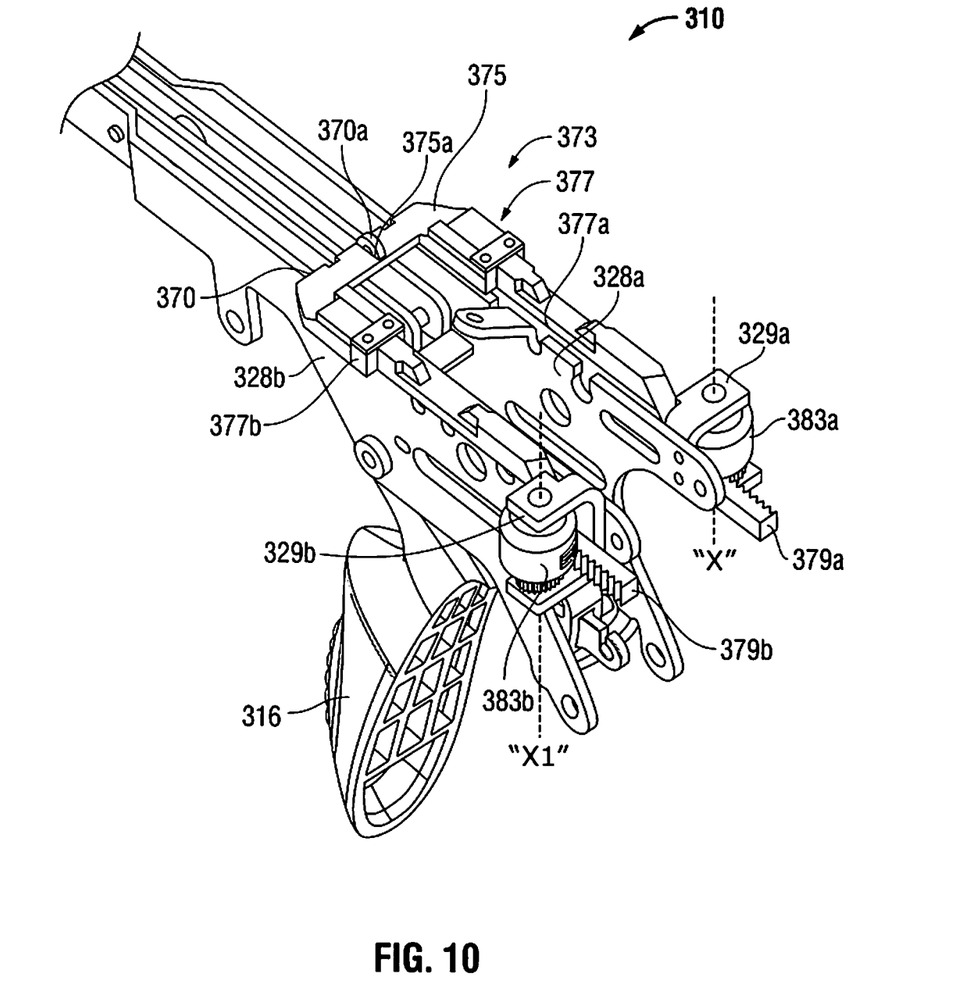
FIG. 10 is a perspective view of portion of the stapler of the present disclosure of an alternate embodiment showing an alternate indicator on a surgical stapler.
Figures 11, 12:
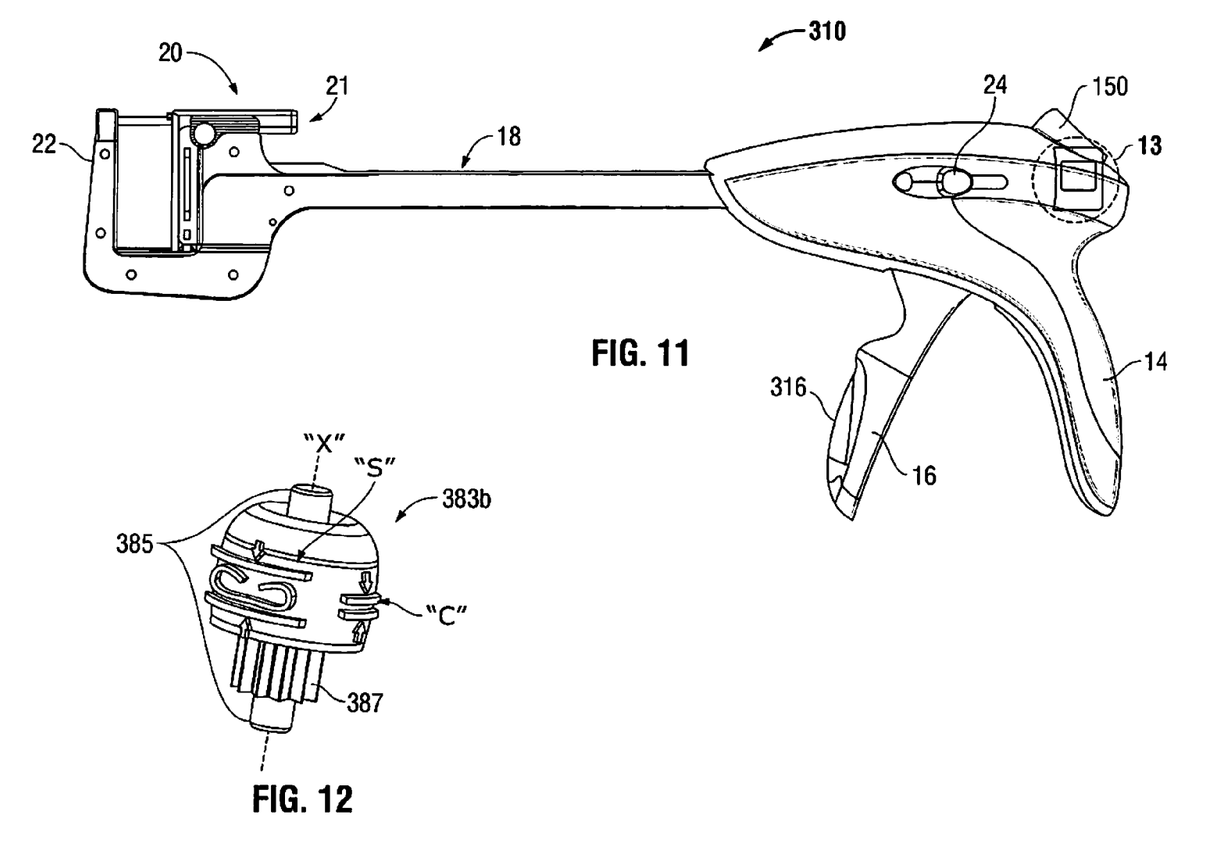
FIG. 11 is a side view of a surgical stapler including the indicator mechanism of FIG. 10.
FIG. 12 is a side view of an indicator member of the indicator mechanism of FIG. 10.

Turning now to FIGS. 10-12, an alternate embodiment of a surgical stapler in accordance with the present disclosure is shown generally as surgical stapler 310. Surgical stapler 310 is substantially similar to surgical stapler 10, and will only be described as relates to the differences therebetween.

Surgical stapler 310 includes an indicator mechanism 373 configured to provide visual indication to a user of the current condition of surgical stapler 310. Indicator mechanism 373 includes a base 375 and a pair of link members 377a, 377b. Base 375 includes a slot 375a configured to be received about flange 370a of thrust bar 370; however, base 375 may be attached with thrust bar 370 in any suitable manner, including adhesive and mechanical connections. Alternatively, indicator mechanism 373 can be integrally formed with thrust bar 370. Link members 377a, 377b extend proximally from base 375 and are configured to slide along frame members 328a, 328b as thrust bar 370 is advanced through an approximation stroke and a stapling stroke. Link members 377a, 377b may be integrally formed with base 375, or instead, may be attached thereto in any suitable manner. Ends of link members 377a, 377b each include toothed extension or rack 379a, 379b. Toothed extensions 379a, 379b may be integrally formed with respective link members 377a, 377b, or instead, may be attached thereto in any suitable manner. As will be discussed in further detail below, toothed extensions 379a, 379b are configured to operably engage indicator members 383a, 383b.

With continued reference to FIG. 10, indicator mechanism 373 includes indicator members 383a, 383b operably mounted on a distal end of frame members 328a, 328b. As shown, indicator members 383a, 383b include pinion members rotatably supported on pinion holders 329a, 329b. In one embodiment, and as shown, pinion holders 329a, 329b are securely mounted to proximal ends of respective frame members 328a, 328b using rivets; however any suitable fastening means may be used. In alternate embodiments, pinion holders 329a, 329b are integrally formed with frame members 328a, 328b and may be positioned in other locations along body 12.

Figure 13:
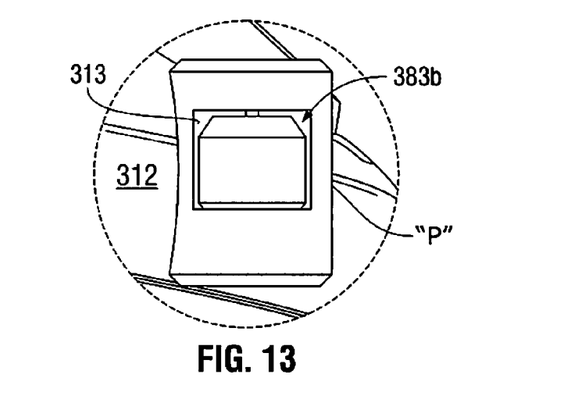
FIG. 13 is an enlarged view of the indicated area of detail of FIG. 11 showing a pre-clamp symbol.
Figure 14:
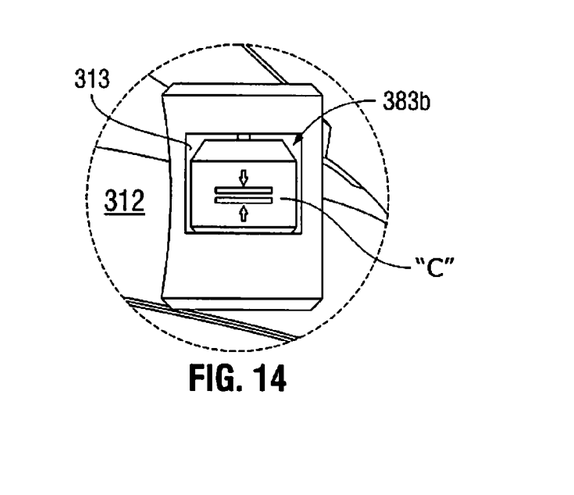
FIG. 14 is an enlarged view of the indicated area of detail of FIG. 11 showing a clamp symbol.
Figure 15:
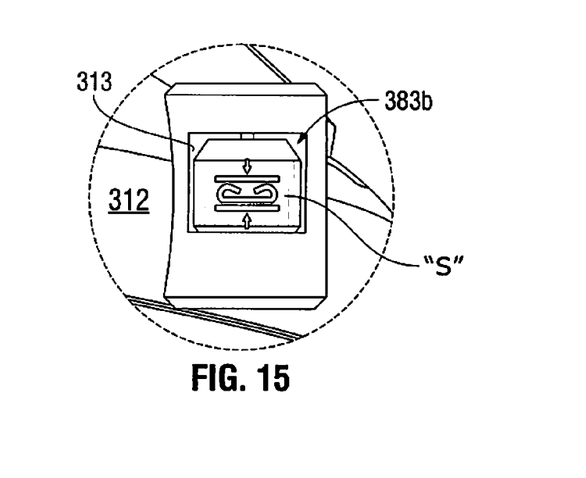
FIG. 15 is an enlarged view of the indicated area of detail of FIG. 11 showing a stapled (fired) symbol.

Turning now to FIG. 12, indicator member 383b is shown. Indicator members 383a, 383b are substantially similar and include an axle 385 defining a longitudinal axis "X" and a toothed gear 387. Axles 385 of indicator members 383a, 383b are perpendicular to the longitudinal axis of the thrust bar and are configured such that indicator members 383a, 383b are rotatably received by respective pinion holders 329a, 329b. Toothed gears 387 are configured to engage toothed extensions 379a, 379b formed on link members 377a, 377b, respectively. Each of indicator members 383a, 383b include a pre-clamp symbol "P" (FIG. 13), a clamp symbol "C" (FIG. 14) and a staple symbol "S" (FIG. 15). Symbols "P", "C", "S" can be arranged about indicator member 383b in a clockwise configuration while symbols "P", "C", "S" arranged about indicator members 383a in a counter-clockwise configuration. Other symbols or indicia are also contemplated.

Surgical stapler 310 includes a body 312 including a pair of windows 313. Windows 313 are configured to align with indicator members 383a, 383b such that each symbols "P", "C", "S" may be sequentially viewed during firing of surgical stapler 310. The mirror image configuration of symbols "P", "C", "S" are such that the same symbol is viewed in both of windows 13 during use of surgical stapler 310.

Surgical stapler 310 and indicator mechanism 373 operate in a substantially similar manner to surgical stapler 10 described herein above. Prior to an approximation stroke, pre-clamp symbols "P" of indicator members 383a, 383b are visible through windows 313. During the approximation stroke, thrust bar 370 is advanced distally causing the advancement of base 375, link members 377a, 377b, and toothed extension 379a, 379b (collectively, rack 377). Advancement of toothed extensions 379a, 379b cause rotation of respective indicator members 383a, 383b. Following the approximation stroke, clamp symbols "C" are visible through windows 313. Release of trigger 16 permits trigger 16 to return to a non-compressed condition to permit the stapling stroke. During the stapling stroke, thrust bar 370 is advanced further distally, thereby causing the advancement of base 375, link members 377a, 377b, and toothed extension 379a, 379b, and the rotation of respective indicator members 383a, 383b. Following the stapling stroke, staple symbols "S" on indicator members 383a, 383b are visible through windows 313. If at any time during the stapling process surgical stapler 310 is not in desired stage or condition, one of symbols "P", "C", "S" will not be completely visible through window 313, thereby providing a clinician with visual indication that surgical stapler 310 is not in such stage.

It will be understood that various modifications may be made to the embodiments disclosed herein. For example, the components of the surgical stapling device can be formed of any material suitable for surgical use and having the required strength characteristics. The stapling device could contain two part fasteners. Therefore, the above description should not be construed as limiting, but merely as exemplifications of preferred embodiments. Those skilled in the art will envision other modifications within the scope and spirit of the claims appended hereto.

What is claimed is:
1. A surgical stapler comprising:
   a body;
   a stapling assembly positioned on a distal portion of the body, the stapling assembly including a cartridge assembly and an anvil assembly;
   a thrust bar slidably disposed within the body and configured to advance distally from a retracted position to a first advanced position during approximation of the cartridge assembly towards the anvil assembly and advance further to a second advanced position to cause the release of staples from the cartridge assembly; and at least one indicator member connected to the thrust bar and configured to provide visual indication to a user upon complete approximation of the cartridge assembly and upon release of staples from the cartridge assembly, wherein the at least one indicator member includes a base and a pair of extensions extending from the base, the extensions including a visual indicator to provide the visual indication to the user, wherein the extensions extend laterally beyond the thrust bar.

2. The surgical stapler of claim 1, wherein a distal end of the thrust bar is configured for operable engagement with the stapling assembly to cause the ejection of staples from the cartridge assembly during the release of staples from the cartridge assembly.

3. The surgical stapler of claim 1, wherein the body includes at least one window for viewing the indicator member.

4. The surgical stapler of claim 1, wherein the indicator member is further configured to indicate that the cartridge assembly is ready to be approximated towards the anvil assembly.

5. The surgical stapler of claim 1, wherein the indicator member is slidably mounted within the body.

6. The surgical stapler of claim 1, wherein the indicator member is rotatably mounted within the body.

7. The surgical stapler of claim 1, wherein the indicator member includes a first symbol to indicate completion of the approximation stroke and a second symbol to indicate the release of staples from the cartridge assembly.

8. The surgical stapler of claim 1, wherein the indicator member is rotatably mounted with respect to the thrust bar.

9. The surgical stapler of claim 8, further comprising a rack operably connected to the thrust bar and having a pair of toothed extensions, the toothed extensions being operably engaged with the indicator member and advancement of the thrust bar causes rotation of the indicator member.

10. The surgical stapler of claim 9, wherein the rack extends from a base positioned distal of the indicator member, the base being mounted to the thrust bar.

11. The surgical stapler of claim 9, wherein the rack extends from a base positioned distal of the indicator member, the base being mounted to the thrust bar.

12. The surgical stapler of claim 1, wherein the indicator member is rotatable about an axis perpendicular to the longitudinal axis of the thrust bar.

13. A surgical stapler comprising;
a body;
a stapling assembly positioned on a distal portion of the body, the stapling assembly including a cartridge assembly and an anvil assembly;
a thrust bar slidably disposed within the body and configured to advance distally from a retracted position to a first advanced position;
an indicator member including a first symbol configured to provide visual indication to a user upon complete approximation of the cartridge assembly towards the anvil assembly and a second symbol configured to provide visual indication to the user upon release of staples from the cartridge assembly; and
a rack operably connected to the thrust bar and having a toothed extension, the toothed extension being operably engaged with the indicator member, wherein advancement of the thrust bar causes rotation of the indicator member.

14. The surgical stapler of claim 13, wherein the indicator member is further configured to indicate the stapler is ready to be approximated.

15. The surgical stapler of claim 13, wherein the indicator member is rotatable about an axis perpendicular to a longitudinal axis of the thrust bar.

16. The surgical stapler of claim 13, wherein the body defines a window configured to permit viewing of the first symbol on the indicator member upon complete approximation of the cartridge assembly and to permit viewing of the second symbol upon release of staples from the cartridge assembly.

17. The surgical stapler of claim 13, wherein the body defines a window configured for individual viewing of the first symbol and the second symbol.

18. The surgical stapler of claim 13, wherein only one of the first symbol and the second symbol is viewable through a window defined by the body at one time.

19. A surgical stapler comprising:
a body;
a stapling assembly positioned on a distal portion of the body, the stapling assembly including a cartridge assembly and an anvil assembly;
a thrust bar slidably disposed within the body and configured to advance distally from a retracted position to a first advanced position during approximation of the cartridge assembly towards the anvil assembly and advance further to a second advanced position to cause the release of staples from the cartridge assembly;
an indicator member connected to the thrust bar, the indicator member including a first symbol configured to provide visual indication to a user upon complete approximation of the cartridge assembly and a second symbol configured to provide visual indication to the user upon release of staples from the cartridge assembly, wherein the indicator member is rotatably mounted with respect to the thrust bar; and
a rack operably connected to the thrust bar and having a toothed extension, the toothed extension being operably engaged with the indicator member,
wherein advancement of the thrust bar causes rotation of the indicator member.

* * * * *